(12) United States Patent
Leuze et al.

(10) Patent No.: US 11,291,852 B2
(45) Date of Patent: Apr. 5, 2022

(54) ACCURATE PATIENT-SPECIFIC TARGETING OF CRANIAL THERAPY USING A BRAIN ATLAS

(71) Applicant: The Board of Trustees of the Leland Stanford Junior University, Stanford, CA (US)

(72) Inventors: Christoph Leuze, Palo Alto, CA (US); Jennifer McNab, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 348 days.

(21) Appl. No.: 16/269,407

(22) Filed: Feb. 6, 2019

(65) Prior Publication Data

US 2019/0240499 A1    Aug. 8, 2019

Related U.S. Application Data

(60) Provisional application No. 62/626,929, filed on Feb. 6, 2018.

(51) Int. Cl.
*A61N 2/00* (2006.01)
*A61N 2/02* (2006.01)
(Continued)

(52) U.S. Cl.
CPC ............ *A61N 2/006* (2013.01); *A61B 5/0077* (2013.01); *A61B 5/6803* (2013.01); *A61N 2/02* (2013.01);
(Continued)

(58) Field of Classification Search
CPC ........ A61N 2/006; A61N 2/02; A61B 5/0077; A61B 5/6803; A61B 2576/026; A61B 5/0064; A61B 5/6814; A61B 5/0042; A61B 5/4064; A61B 5/055; A61B 2034/2057; G06T 7/0012; G06T 2207/30016; G06T 7/70; G06T 7/73; G06T 7/74;
(Continued)

(56) References Cited

U.S. PATENT DOCUMENTS 6,167,295 A    12/2000  Cosman
7,783,132 B2 *  8/2010  Nowinski .................. G06T 7/35
                                              382/294
(Continued)

FOREIGN PATENT DOCUMENTS

EP    2684518    1/2014

OTHER PUBLICATIONS

NPL Search History (Year: 2021).*
(Continued)

*Primary Examiner* — Nancy Bitar
(74) *Attorney, Agent, or Firm* — Lumen Patent Firm (57) ABSTRACT

Improved targeting of cranial therapy is provided by warping a general purpose brain atlas to a measured head shape of the patient. The resulting patient-specific transformation from brain atlas to patient's head allows one to estimate the location of brain features of the patient without any patient specific brain imaging. Such cost-effective targeting of brain features is especially useful for therapies like transcranial magnetic stimulation, where accuracy of targeting brain structures and session-to-session consistency are both important.

14 Claims, 12 Drawing Sheets

(51) Int. Cl.
*G06T 7/00* (2017.01)
*A61B 5/00* (2006.01)
*A61B 5/055* (2006.01)

(52) U.S. Cl.
CPC .......... *G06T 7/0012* (2013.01); *A61B 5/0042* (2013.01); *A61B 5/0064* (2013.01); *A61B 5/055* (2013.01); *A61B 5/4064* (2013.01); *A61B 5/6814* (2013.01); *A61B 2576/026* (2013.01); *G06T 2207/30016* (2013.01)

(58) Field of Classification Search
CPC ........... G06T 9/002; G06T 2207/20081; G06T 2207/20084; G06F 3/013
See application file for complete search history.

(56) References Cited

U.S. PATENT DOCUMENTS

| | | | | |
|---|---|---|---|---|
| 8,050,475 | B2 * | 11/2011 | Nowinski | A61B 6/504 382/130 |
| 8,125,223 | B2 * | 2/2012 | K.N. | G06T 7/136 324/309 |
| 8,314,815 | B2 | 11/2012 | Navab | |
| 8,588,491 | B2 * | 11/2013 | Ikeda | A61B 6/501 382/131 |
| 8,774,481 | B2 * | 7/2014 | Schreibmann | G06T 7/30 382/131 |
| 9,715,753 | B2 | 7/2017 | Berry | |
| 10,074,173 | B2 * | 9/2018 | Miller | A61B 6/037 |
| 2005/0113630 | A1 * | 5/2005 | Fox | A61N 2/006 600/13 |
| 2009/0220136 | A1 * | 9/2009 | Bova | A61B 6/5247 382/131 |
| 2010/0185042 | A1 | 7/2010 | Schneider | |
| 2012/0314924 | A1 | 12/2012 | Carlton | |
| 2013/0345491 | A1 | 12/2013 | Saitoh | |
| 2014/0179981 | A1 * | 6/2014 | Katz | A61N 2/006 600/15 |
| 2015/0099252 | A1 | 4/2015 | Anderson | |
| 2015/0119689 | A1 | 4/2015 | Pascual-Leone | |
| 2016/0256069 | A1 * | 9/2016 | Jenkins | A61B 34/74 |
| 2016/0284132 | A1 | 9/2016 | Kim | |
| 2017/0128737 | A1 * | 5/2017 | Yasumuro | G01S 17/89 |

OTHER PUBLICATIONS

Leuze et al., "Depth sensing for atlas-to-head shape registration for augmented reality transcranial magnetic stimulation (arTMS)" Oct. 11, 2018, Stanford Neuroscience Symposium.

Pietrzyk et al., "An interactive technique for 3-D image registration: validation for PET, SPECT, MRI and CT brain studies", 1994, J. Nuclear Medicine v35n12, pp. 2011-2018.

Besl et al., "Method for registration of 3-D shapes", 1991, Proc. SPIE v1611.

Newcombe et al, "KinectFusion: Real-Time Dense Surface Mapping and Tracking", 2011.

Clausner et al., "Photogrammetry-Based Head Digitization for Rapid and Accurate Localization of EEG/Electrodes and MEG Fiducial Markers Using a Single Digital SLR Camera", 2017, Frontiers in Neuroscience v11, article 264.

Murthy et al., "Faster and improved 3-D head digitization in MEG using Kinect", 2014, Frontiers in Neuroscience v8, article 326.

Hughes et el., "A flexible infrastructure for delivering Augmented Reality enabled Transcranial Magnetic Stimulation", 2006, Studies in health technology and informatics.

Koessler et al., "EEG-MRI Co-registration and Sensor Labeling Using a 3D Laser Scanner", 2011, Annals of Biomedical Engineering, v39n3, p. 983.

Min et al., "Real-Time 3D Face Identification from a Depth Camera", 2012, 21st International Conference on Pattern Recognition.

Toga et al., "The role of image registration in brain mapping", 2001, Image Vis Comput. v19n1-2, pp. 3-24.

Soeiro et al., "Mobile Solution for Brain Visualization Using Augmented and Virtual Reality", 2016, 20th International Conference Information Visualisation.

Author unknown, "Tutorial", 2018.

Yasumuro et al., "Coil Positioning System for Repetitive Transcranial Magnetic Stimulation Treatment by ToF Camera Ego-Motion", 2013, 35th Annual International Conference of the IEEE EMBS.

* cited by examiner

702 — 3D camera measures location and orientation of patient's head by measuring facial landmarks or by measuring facial point cloud 704 — Location of brain region of interest for the patient is estimated from a brain atlas 706 — TMS coil(s) are placed at desired orientation over the brain region of interest based on its location estimate 708 — Marker attached to TMS coil(s) (or direct tracking of TMS coil(s)) allows system to measure transformation and rotation of TMS coil(s) relative to the facial landmarks or facial point cloud 710 — Transformation and rotation of TMS coil(s) with respect to the the facial landmarks or facial point cloud is saved to a database

902 — 3D camera measures location and orientation of patient's head by measuring facial landmarks or by measuring facial point cloud 904 — Facial landmarks or facial point cloud is compared with database and the corresponding TMS coil location and orientation from the first session is retrieved 906 — The location and orientation of the TMS coil is presented to the clinician (e.g., with a 2D screen or an augmented reality display) to allow precise reproduction of the TMS coil location and orientation from the first session

ACCURATE PATIENT-SPECIFIC TARGETING OF CRANIAL THERAPY USING A BRAIN ATLAS

CROSS REFERENCE TO RELATED APPLICATIONS

This application claims the benefit of U.S. provisional patent application 62/626,929, filed on Feb. 6, 2018, and hereby incorporated by reference in its entirety.

FIELD OF THE INVENTION

This invention relates to improved positioning and consistency for cranial therapy.

BACKGROUND

Many clinical applications such as transcranial magnetic stimulation (TMS) require the clinician to locate internal anatomical regions such as specific brain areas that are not visible to the human eye from the outside. Different approaches such as the "5 cm rule", scalp measurements and marker-based navigation devices exist that allow one to place the TMS coil with varying levels of accuracy. However, all current techniques that increase targeting accuracy beyond the standard "5 cm rule" increase setup time and require extra training for the clinician. Due to the regular treatment schedule with 20-30 treatment sessions, most TMS operators therefore stick to the fast but inaccurate "5 cm rule" targeting method. This leads to two distinct problems: 1) poor accuracy of the therapy relative to the brain structures being targeted for treatment, and 2) poor consistency of the targeting between various therapy sessions. Accordingly, it would be an advance in the art to alleviate these difficulties in a cost-effective manner.

SUMMARY

Cost effective and accurate targeting of cranial therapy is provided by taking measurements of the patient's head shape, and then fitting a brain atlas to these head measurements to provide customized targeting to brain structures of the patient. In this manner, expensive imaging for targeting, such as magnetic resonance imaging (MRI), can be avoided. This approach can be further improved by measuring therapy device locations relative to the patient's face (either facial landmarks and/or a facial point cloud). By saving this information in a database and using it to position the therapy devices in subsequent therapy sessions, consistency of therapy targeting from one session to the next is improved.

This approach further allows one to track and save therapy device location and orientation without the need for a prior MRI scan, allowing one to collect valuable data that allows one to relate therapy device targeting with treatment outcome. Such a dataset that contains head shape, coil placement and treatment outcome can then be used to develop more effective therapy protocols.

One application for this approach is to transcranial magnetic stimulation. TMS is a clinical treatment for depression where the same localized brain region needs to be treated 5 times a week over the course of 4-6 weeks. The recurring need to localize the same brain area makes it an ideal application for this approach. However, the same principles can be extended to any other kind of cranial therapy, such as temporally interfering electric field therapy.

Significant advantages are provided. Currently the localization of internal anatomical regions for TMS is either based on very generalized atlases such as the most commonly used "5 cm rule", leading to an imprecise localization that varies strongly between treatment sessions and has been shown to decrease treatment efficacy. The current alternatives are time-consuming scalp measurements that do not allow one to consistently reproduce coil orientation or expensive and difficult to use marker-based neuronavigation equipment that needs several minutes of setup before and during each treatment session.

With the present approach, the internal anatomical location only has to be calibrated to the head coordinate system once during the initial treatment session, and this is efficiently done by warping a brain atlas as needed to fit head measurements from the patient. Registration of facial landmarks and/or a facial point cloud to TMS coil positions efficiently provides improved consistency of treatment locations for all treatments in the treatment plan.

To summarize, significant advantages provided by the present approach include: Low cost; Ease-of-use compared to current marker-based clinical navigation devices; Short setup time; and Increased consistency, accuracy and treatment outcome compared to no navigation or scalp measurements.

DETAILED DESCRIPTION

Figure 1:
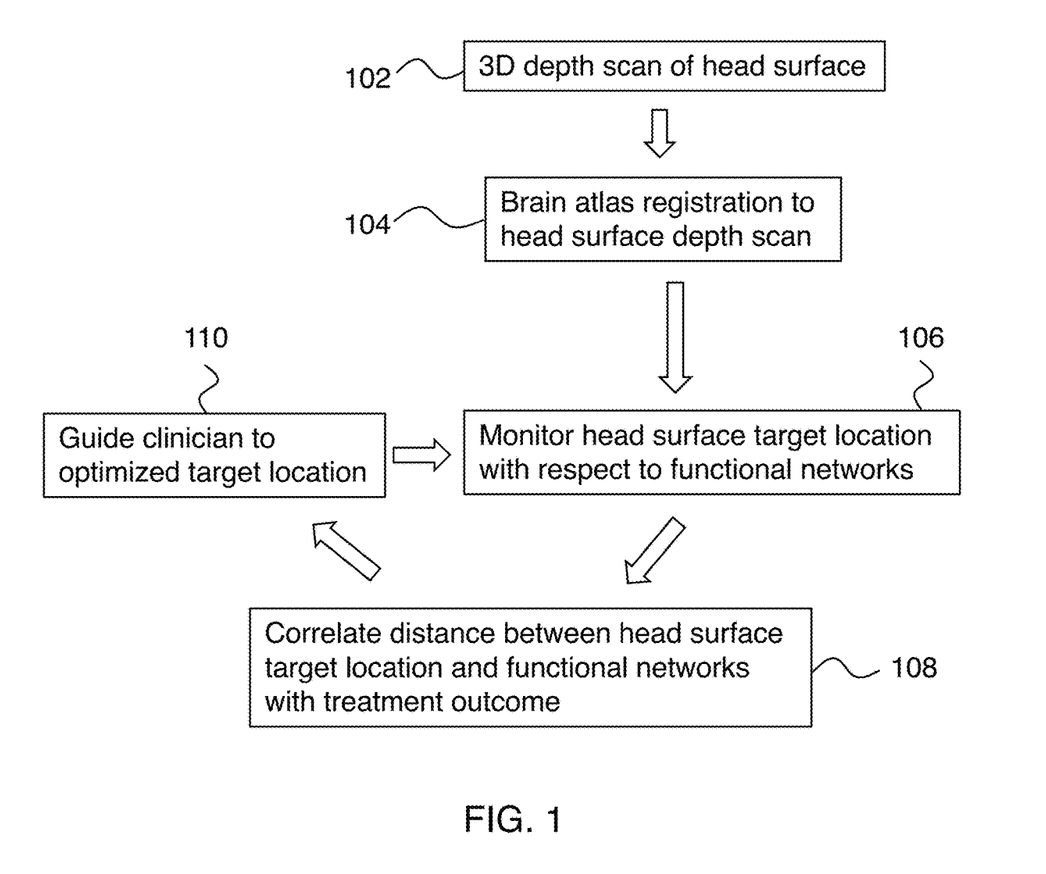
FIG. 1 is a flow diagram relating to embodiments of the invention.

FIG. 1 is a flow diagram relating to embodiments of the invention. An overview of this process is as follows. Step 102 is obtaining a 3D depth scan of the patient's head surface. Step 104 is registering a brain atlas to the 3D head surface depth scan. Step 106 is monitoring head surface target location relative to functional networks in the brain (that are to be treated). Step 108 is correlating distance between head surface target location and functional networks with treatment outcome. Step 110 is guiding the clinician to optimized target locations.

As indicated on FIG. 1, steps 102 and 104 are preliminary, and steps 106, 108, 110 could be repeated as needed as part of a research program. Thus FIG. 1 is an exemplary larger setting within which the invention may be practiced, and the invention itself relates mainly to steps 102, 104 of this figure.

More specifically, an exemplary embodiment of the invention is a method of targeting cranial therapy to a patient. This method includes:

a) providing a brain atlas having coordinates for brain structures, where the brain atlas is a 3D volumetric brain atlas;

b) performing a 3D scan of a head of a patient;

c) registering the brain atlas to the 3D scan of the head of the patient, thereby providing coordinates of the brain structures in a patient coordinate system of the 3D scan of the head of the patient; and d) targeting cranial therapy to the patient according to the coordinates of one or more target brain structures in the patient coordinate system.

Several brain atlases are available in the neuroanatomy research community. Brain atlases of interest for this work are 3D volumetric brain atlases which provide 3D information on locations of brain structures (which can be defined functionally and/or anatomically) in the atlas coordinates. Such brain atlases are compilations of results from many representative instances of relevant brain data. Therefore it is not expected that such a brain atlas would precisely match the brain of any specific patient. Mapping the brain atlas to individual patients is how this issue is dealt with, and is described in greater detail below. Briefly, the brain atlas can be warped to the head using a non-linear surface matching algorithm. This warped atlas can then deliver an estimate of the location of the brain region of interest without the need for manual scalp measurements or prior MRI.

This approach is applicable to any kind of cranial therapy, including but not limited to: transcranial magnetic stimulation and temporally interfering electric field therapy.

Figure 2A:
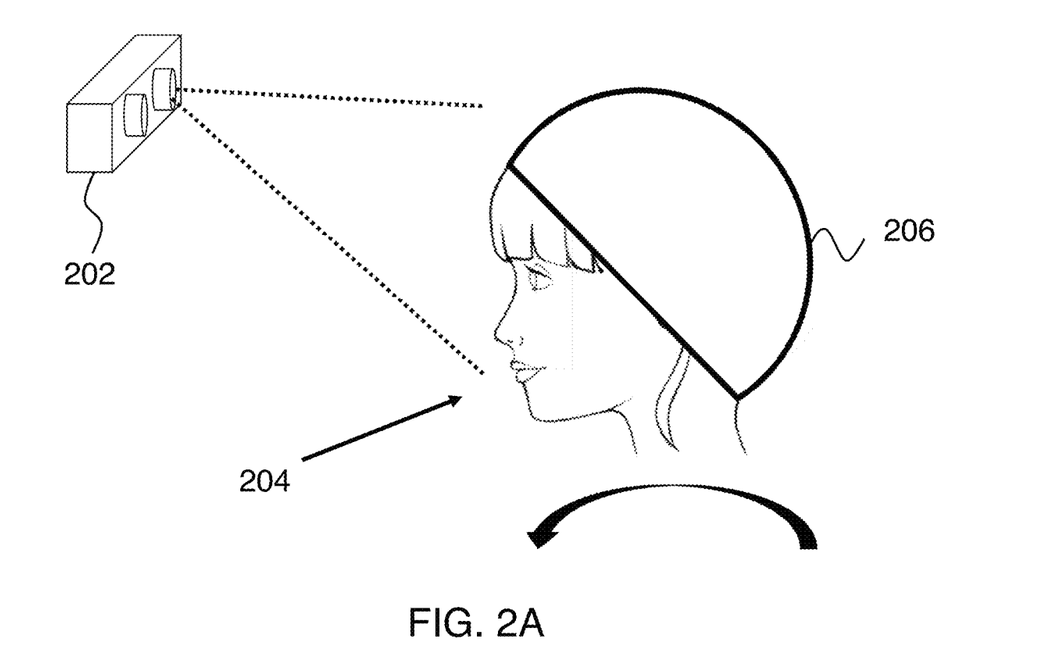
FIGS. 2A-B schematically show making head shape measurements in connection with embodiments of the invention.
Figure 2B:
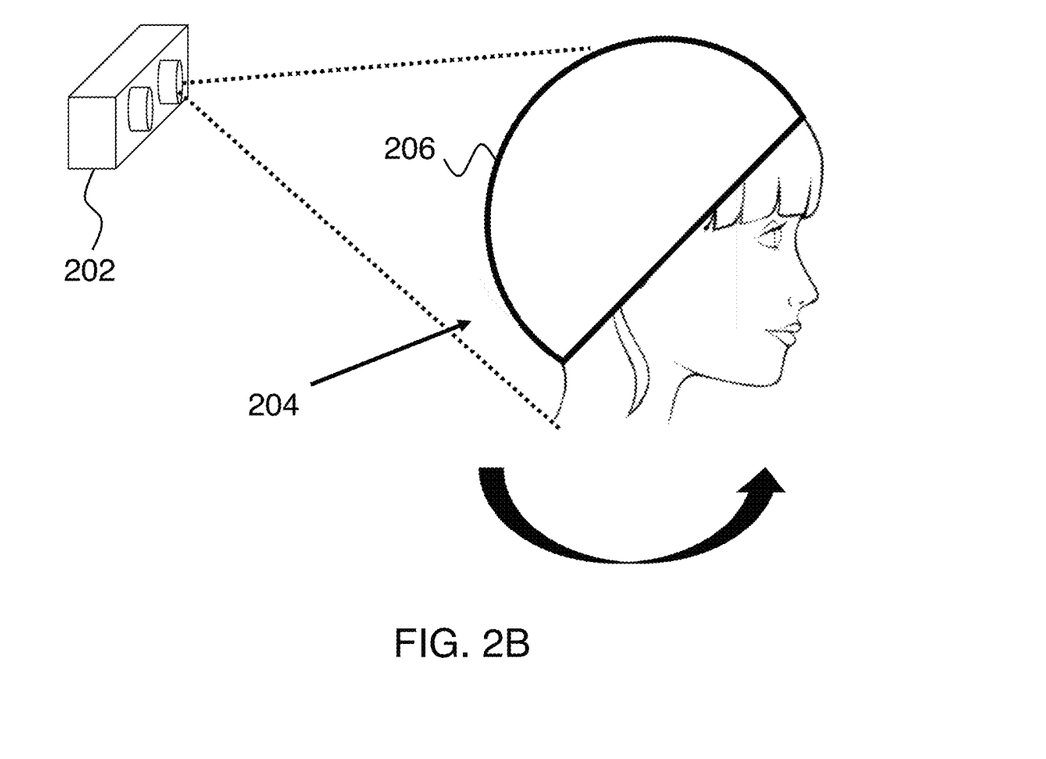

FIGS. 2A-B schematically show making head shape measurements in connection with embodiments of the invention. Here camera 202 measures the full head shape of patient 204. Preferably the effect of hair on head shape is minimized by use of a cap 206 (e.g., a swim cap or the like). FIGS. 2A-B schematically show use of a front view and a back view to get full head shape information. Alternatively, multiple cameras can be used to obtain this information without needing the patient to change position.

Preferably camera 202 is a depth camera (e.g., an RGBD camera providing RGB color channels and a Depth channel). Instead of a depth camera, improved computer vision algorithms can make it possible to perform the same task (optical depth imaging) with a stereoscopic or even single RGB camera. Suitable image processing algorithms for this task are known in the art (e.g., Kinect® fusion algorithm). Tracing the head surface with a marker on cap 206 can optionally be done to improve the quality of the head shape measurements.

Figure 3A:
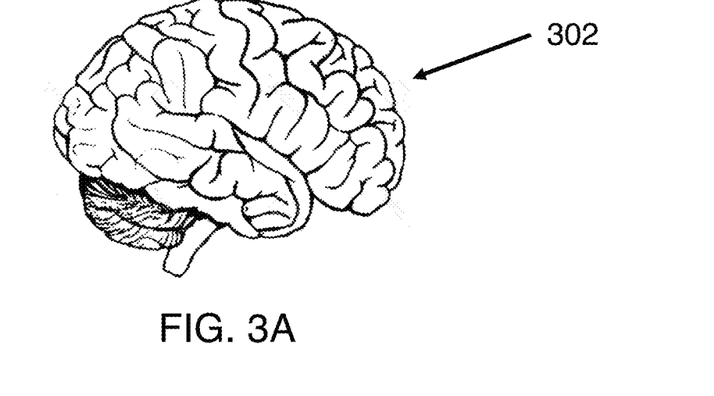
FIGS. 3A-C schematically show warping a brain atlas to match patient head shape measurements.
Figure 3B:
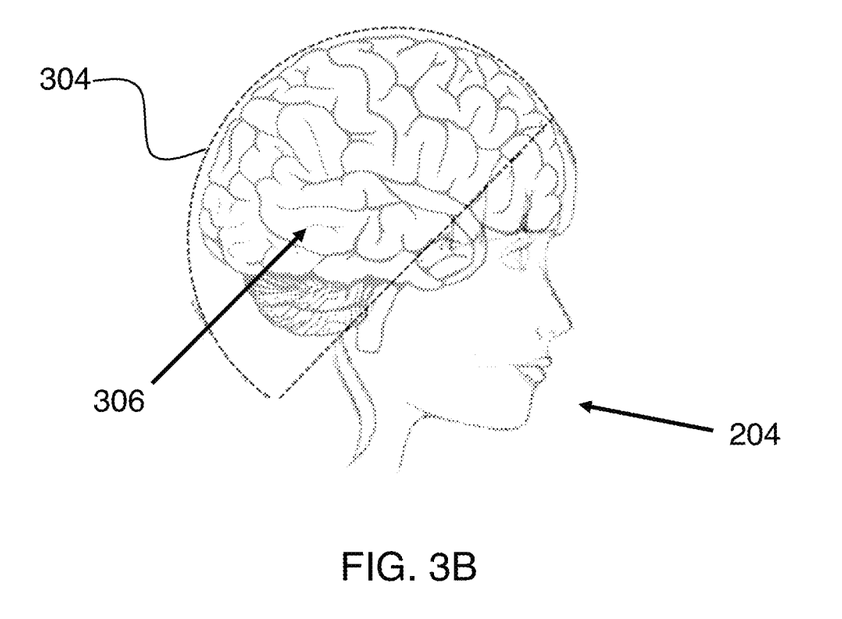
Figure 3C:
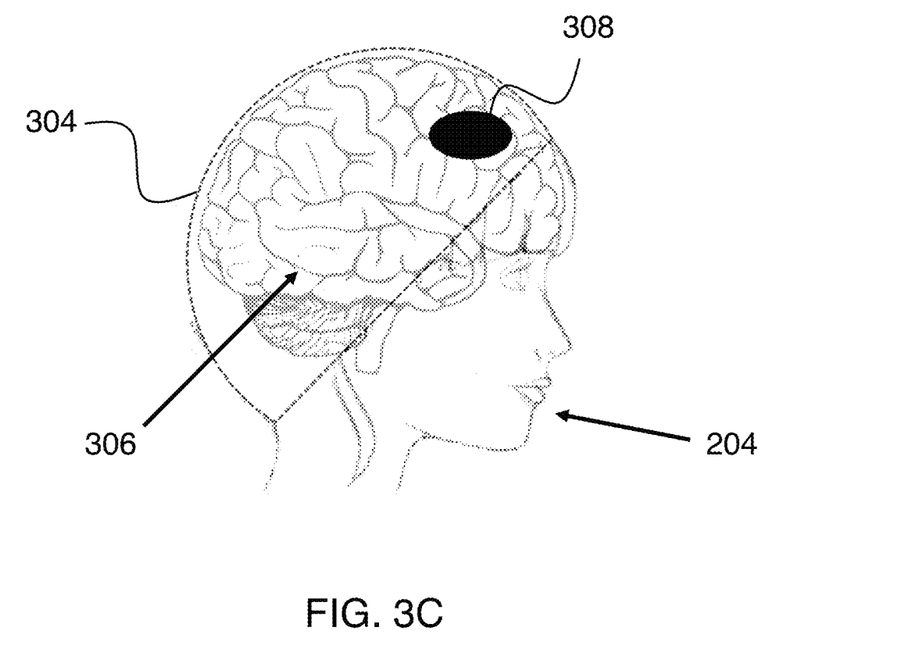

FIGS. 3A-C schematically show warping a brain atlas to match patient head shape measurements. Here 302 on FIG. 3A is the brain atlas before any processing. 304 on FIG. 3B is the head surface shape obtained from the 3D scan of the head of patient 204. The result of fitting brain atlas 302 to head surface shape 304 is schematically shown by 306 on FIG. 3B. Once this is done, the location of a region of interest 308 on FIG. 3C for patient 204 is obtained by taking the coordinates of region of interest 308 in the atlas coordinates, known from the atlas, and applying the atlas->patient transformation on these coordinates. The result is the location of region of interest 308 in patient coordinates. Since the patient coordinates have the head surface shape 304 as a readily available reference, the end result is that treatment can be accurately targeted to region of interest 308 without the need for any individualized imaging of the brain of patient 204.

The registering the brain atlas to the 3D scan of the head of the patient can include performing an affine transformation of the brain atlas to best fit the 3D scan of the head of a patient. In a preferred embodiment, further steps of this part of the method can include voxelizing the 3D scan of the head of the patient to a binary 3D volume to provide a voxelized head scan and/or using externally visible anatomical landmarks such as the nasian, tragi, inian, apex or eyes as landmarks to help determine the best fit for a landmark based affine transformation. The thickness of skull and scalp is accounted for in the brain atlas, so the shape fitting is of the scalp surface in the atlas to the measured scalp surface of the patient.

Figure 4A:
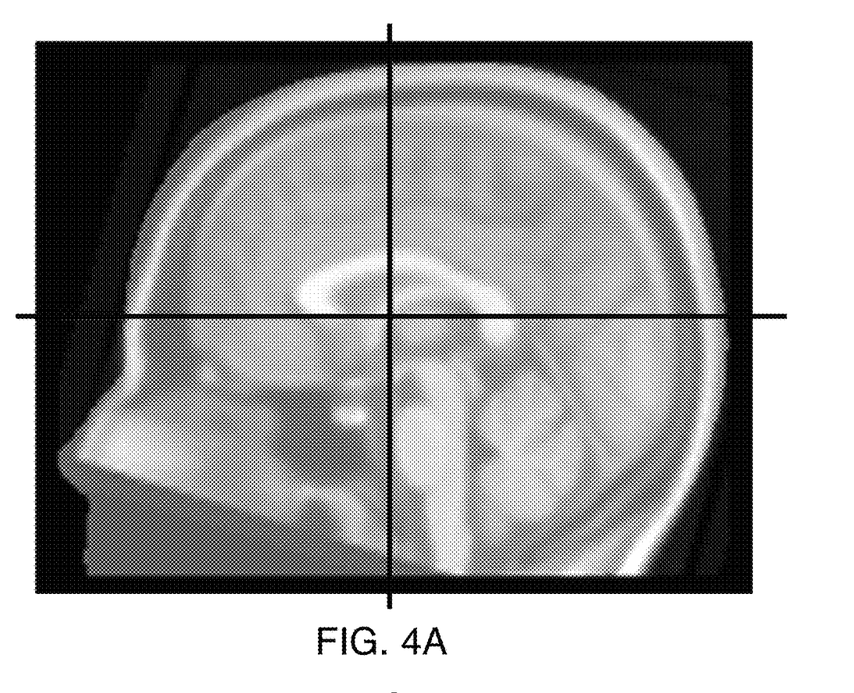
FIG. 4A is an example of a brain atlas image after registering the atlas to patient head shape measurements.
Figure 4B:
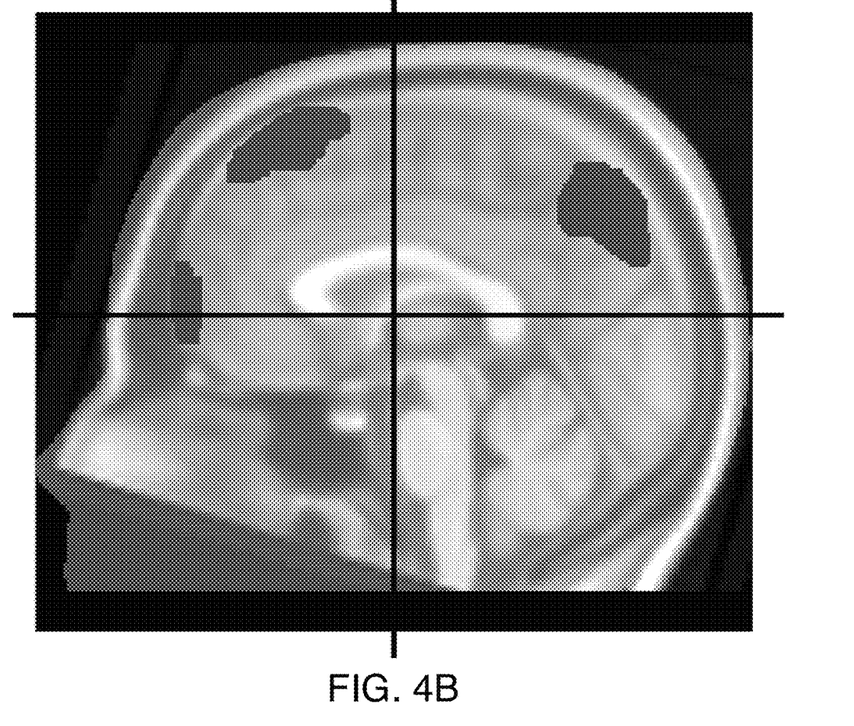
FIG. 4B shows (in gray shading) a functional network in a brain atlas image.

FIG. 4A is an example of a brain atlas image after registering the atlas to patient head shape measurements. FIG. 4B shows (in gray shading) a functional network in the registered brain atlas image of FIG. 4A.

Figure 5A:
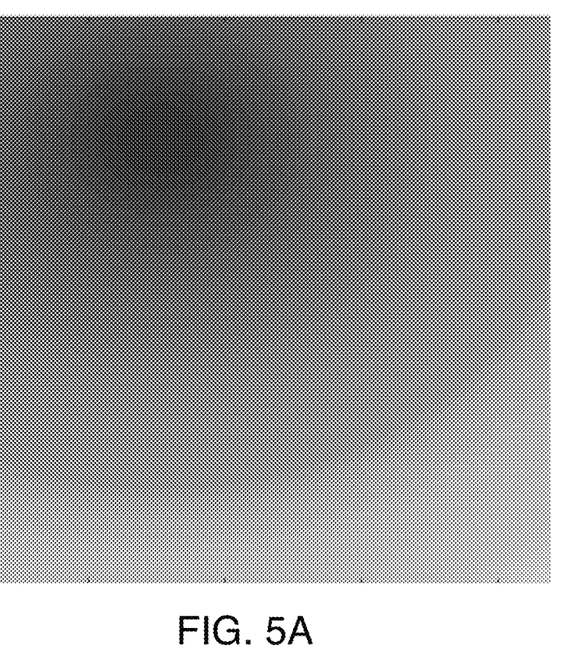
FIG. 5A is an image showing distance from a functional node of interest.
Figure 5B:
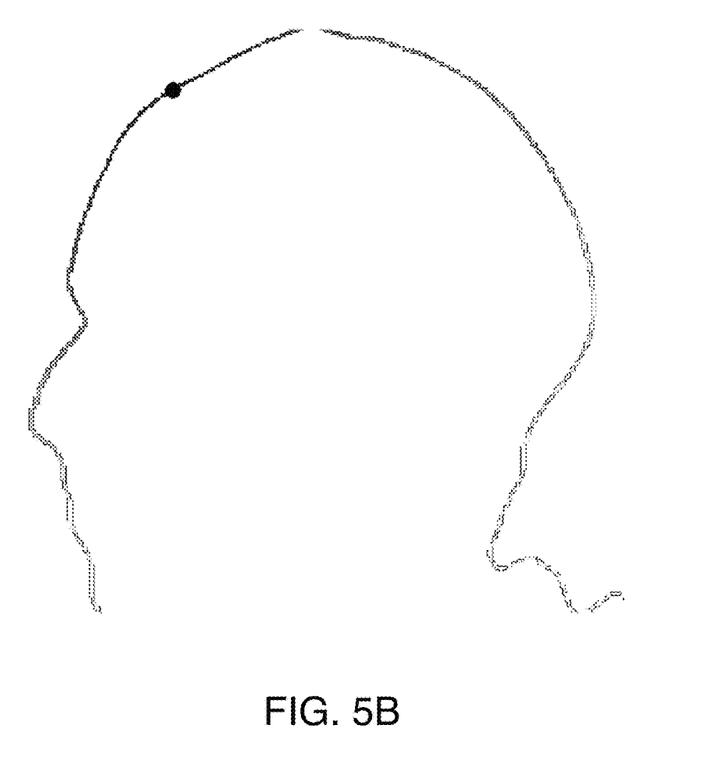
FIG. 5B shows the result of intersecting the distance function of FIG. 5A with the edge of the head.
Figure 5C:
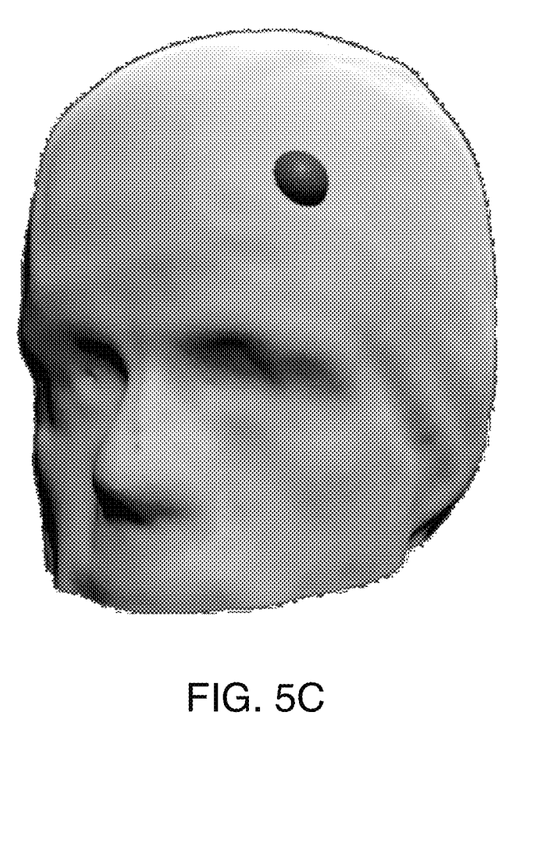
FIG. 5C shows an image of the resulting closest scalp point to the functional node of interest.

FIG. 5A is an image showing distance from a functional node of interest (i.e., a brain region to be treated). This is a simple schematic with smaller distances being shaded darker. FIG. 5B shows the result of intersecting the distance function of FIG. 5A with the edge of the head. Here the point of least distance on the edge of the head is shown with a black disk. This can be better seen in the 3D image of FIG. 5C, which shows an image of the resulting closest scalp point to the functional node of interest. Again, it should be noted that this information on the location of the functional node of interest is obtained without any imaging of the patient's brain.

Figure 6A:
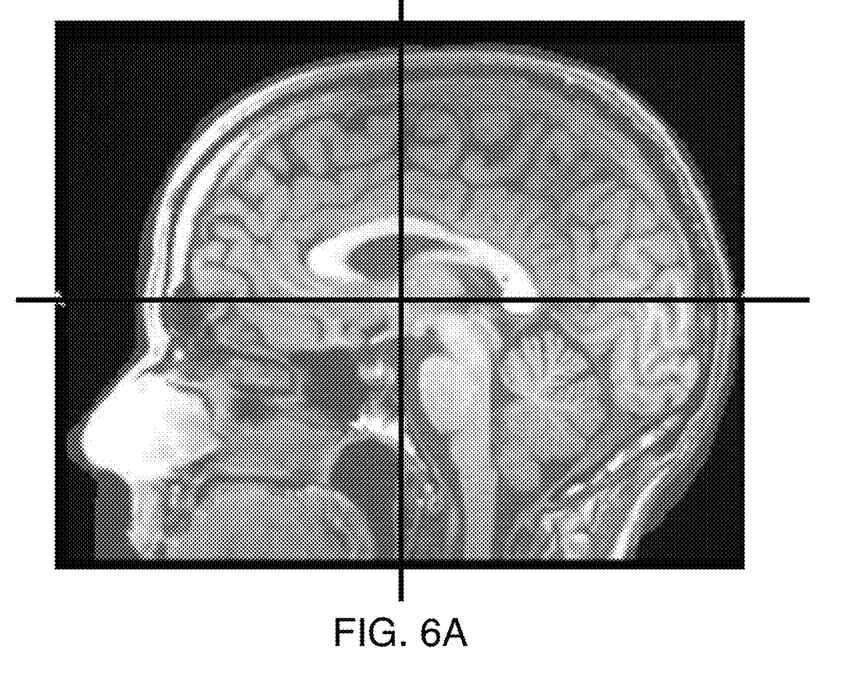
FIGS. 6A-B relate to validation experiments of the present approach.
Figure 6B:
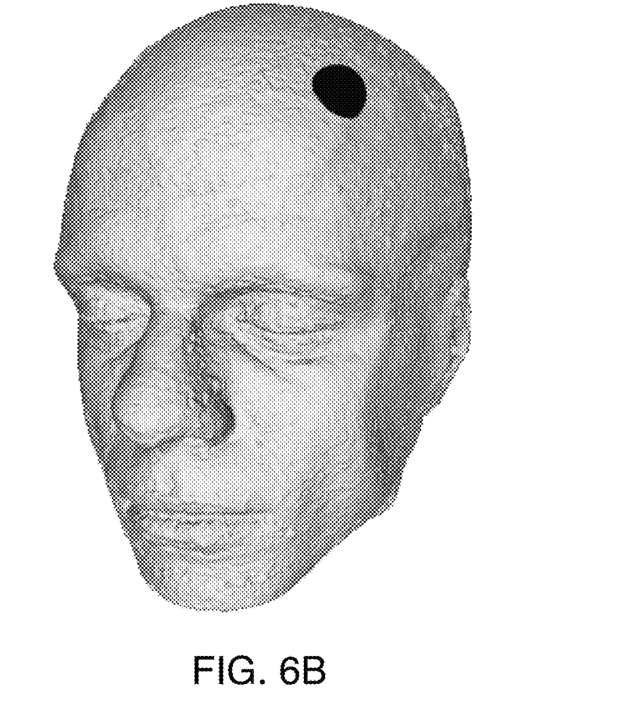

FIGS. 6A-B relate to validation experiments of the present approach. A subject's individual MRI scan was registered to the same subject's 3D depth camera head shape measurement and the location of the closest scalp location to specific cortical areas was compared, leading to a mean error of 14 mm.

Figure 7:
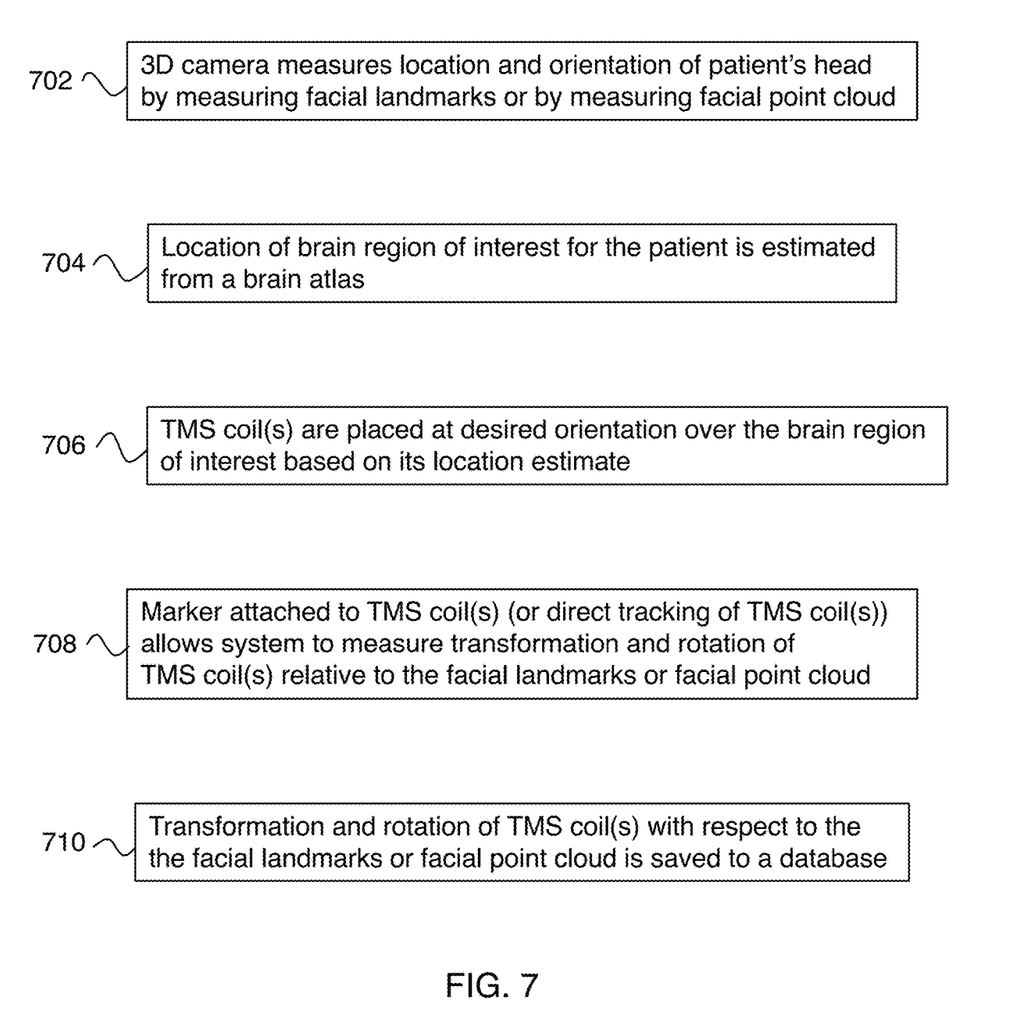
FIG. 7 is a flow diagram relating to an exemplary initial TMS therapy session.

FIG. 7 is a flow diagram relating to an exemplary initial TMS therapy session. In this example, step 702 is performing a 3D optical scan of the patient's head by measuring facial landmarks or by measuring a facial point cloud. Step 704 is estimating the location of a brain region to be treated by using a brain atlas as described above. Step 706 is placing TMS coil(s) to target the brain region of interest, relying on the location estimate of step 704. Step 708 is determining the position and orientation of the TMS coil(s) with respect to the 3D optical scan of step 702. This can be done either by directly tracking the TMS coil locations and/or by placing markers on the TMS coils to improve this location determination. Such markers on the TMS coils are preferably visible in the 3D scan of the head of the patient. Step 710 is saving the TMS coil location information in a database. Typically this database is a patient-specific database of facial features (landmarks and/or point cloud) of the patient relative to positions of TMS coils for delivering the TMS therapy. The database of facial features of the patient relative to positions of TMS coils is preferably used to improve consistency of TMS coil placement from one TMS session to another TMS session.

Figure 8A:
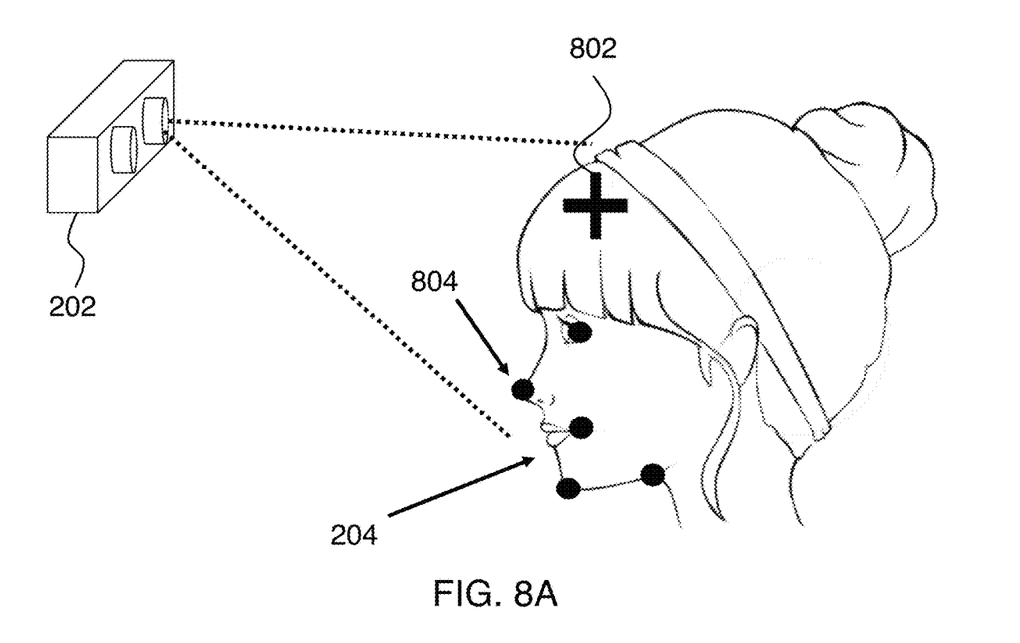
FIGS. 8A-B schematically show the method of FIG. 7.
Figure 8B:
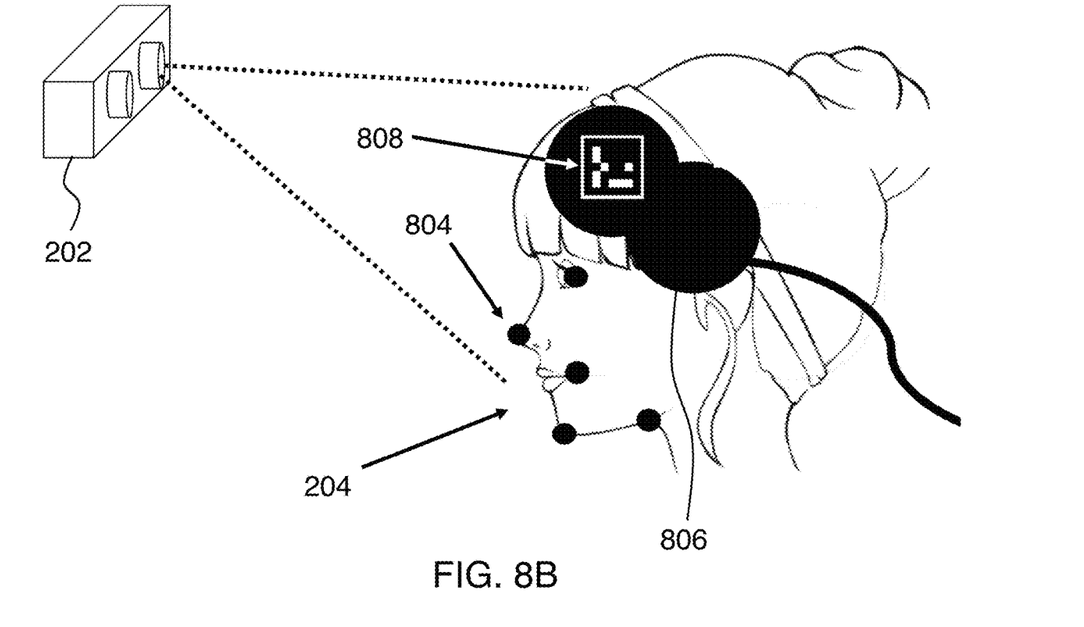

FIGS. 8A-B schematically show the method of FIG. 7. Here 802 is the brain region of interest and 804 schematically shows the facial landmarks (or facial point cloud) used for the 3D optical scan of the patient's head. 806 is a TMS coil and 808 is an optical marker placed on the TMS coil to aid its location determination. Externally visible anatomical landmarks on the patient can be tracked using an RGBD camera (camera with color and depth channel) and a computer vision algorithm that automatically determines the coordinates of these landmarks in world space. These landmarks form a point cloud that spans up a coordinate system in head space. While the external landmark coordinates in head space stay constant, their variation in world space delivers information about the pose of the head. During the first treatment session, the location of the relevant brain region is estimated with a brain atlas as described above and the coil location and orientation with respect to the head landmarks is recorded. Here TMS coil 806 is positioned with respect to brain region of interest 802 according to its location estimate from the brain atlas.

Figure 9:
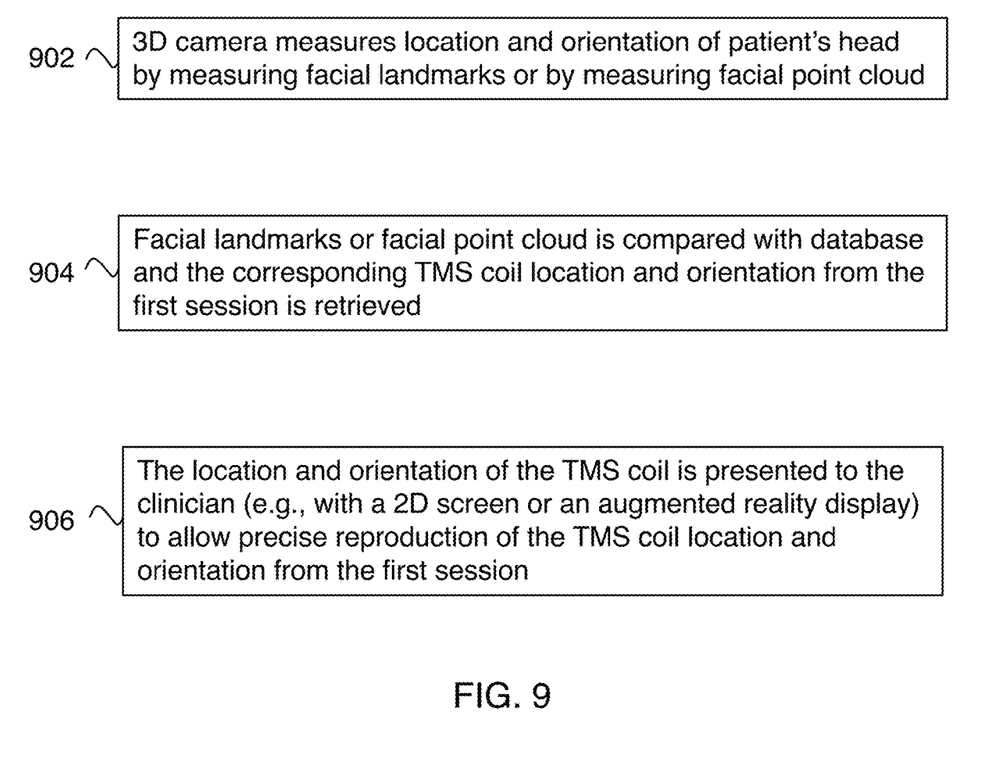
FIG. 9 is a flow diagram relating to an exemplary subsequent TMS therapy session.

FIG. 9 is a flow diagram relating to an exemplary subsequent TMS therapy session. Here step 902 is performing a 3D optical scan of the patient's head by measuring facial landmarks or by measuring a facial point cloud. Step 904 is determining the desired position of the TMS coils with respect to the 3D optical scan based on the database results from the initial TMS treatment. Step 906 is providing a display that allows a user (typically the clinician) to accurately position the TMS coils to reproduce their position and orientation from the initial TMS session. This display can be a conventional 2D display or an augmented reality display, and its main purpose is to facilitate positioning of the TMS coils in accordance with the database.

Figure 10:
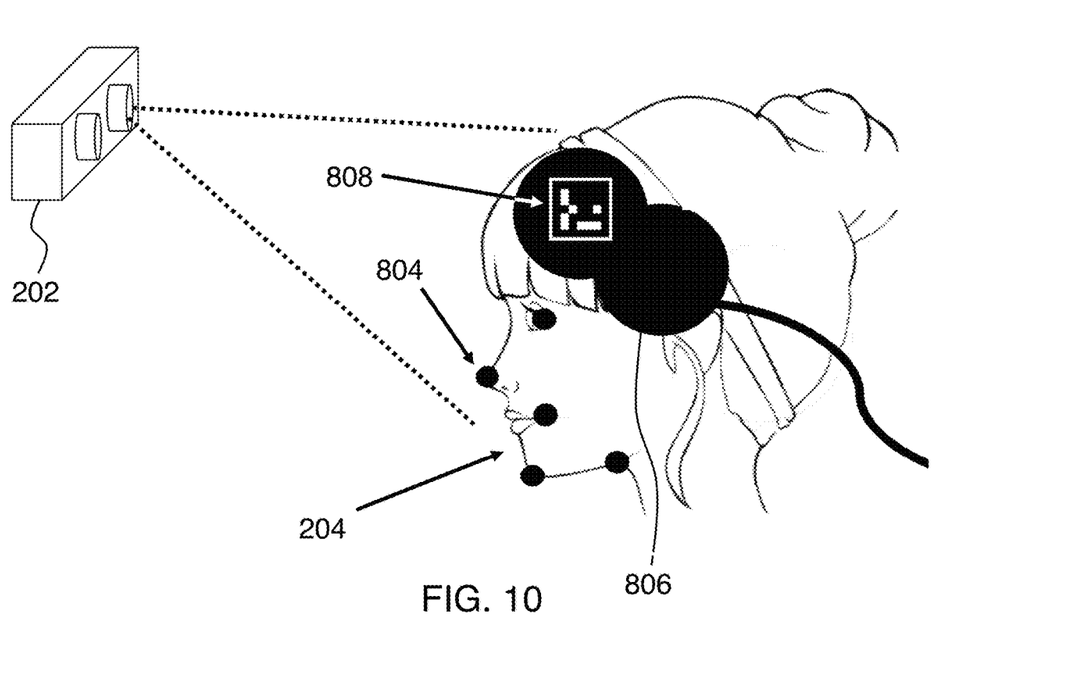
FIG. 10 schematically shows the method of FIG. 9.

FIG. 10 schematically shows the method of FIG. 9. This is similar to FIG. 8B, except that here TMS coil 806 is positioned with respect to brain region of interest 802 according to the database results from the initial session relating TMS coil position and orientation to facial features of the patient.

During follow-up sessions the same camera tracks the head and shows the exact same coil location and orientation from the first treatment session to the TMS operator, allowing him to accurately reproduce the setup of the first treatment session. The head shape and coil positioning is then recorded and saved together with the TMS operator's feedback on patient response or remission values. Data analysis of such a brain stimulation map can then allow one to develop more effective and individualized TMS treatment methods.

Using facial feature tracking this head tracking technique allows one to locate the same scalp location during follow-up sessions within 2.4 mm accuracy for 30 cm camera distance and within 5.8 mm for 60 cm camera distance if the face is looking at the camera within an angle of 20 degrees. These tests have been performed with a low-cost depth sensing camera ($150 Intel Realsense® camera). Higher resolution cameras, such as professional tracking cameras (Optitrack®, $3000+) are expected to improve this accuracy even more. For higher angles of the face with respect to the camera, a point cloud of the face can be measured. Registration of the point cloud to a template of the person's face then allows one to also estimate the head orientation for angles higher than 40 degrees at high accuracy. As a comparison, the common "5 cm rule" has been shown to lead to errors of up to 22 mm for estimating the dorsolateral prefrontal cortex location.

The invention claimed is:

1. A method of targeting cranial therapy to a patient, the method comprising:
obtaining a brain atlas having coordinates for brain structures, wherein the brain atlas is a 3D volumetric brain atlas;
performing an optical 3D scan of a head shape of a patient;
registering the brain atlas to the optical 3D scan of the head shape of the patient, wherein the registering the brain atlas to the optical 3D scan of the head shape of the patient comprises performing an affine transformation of the brain atlas to fit the optical 3D scan of the head shape of the patient, thereby providing coordinates of the brain structures in a patient coordinate system of the optical 3D scan of the head shape of the patient; targeting cranial therapy to the patient according to the coordinates of one or more target brain structures in the patient coordinate system.

2. The method of claim 1, wherein the registering the brain atlas to the optical 3D scan of the head shape of the patient further comprises: voxelizing the optical 3D scan of the head shape of the patient to a binary 3D volume to provide a voxelized head scan, wherein the affine transformation of the brain atlas to fit the voxelized head scan is determined at least in part by reference to externally visible anatomical landmarks.

3. The method of claim 1, wherein an optical depth camera is used to provide the optical 3D scan of the head shape of a the patient.

4. The method of claim 1, wherein the optical 3D scan of the head shape of the patient is provided by multiple optical camera views.

5. The method of claim 1, further comprising having the patient wear a swim cap during the optical 3D scan of the head shape of the patient.

6. The method of claim 1, wherein the targeting cranial therapy to the patient comprises determining one or more closest scalp locations to the one or more target brain structures.

7. The method of claim 1, wherein the cranial therapy is temporally interfering electric field therapy.

8. The method of claim 1, wherein the cranial therapy is transcranial magnetic stimulation (TMS).

9. The method of claim 8, further comprising compiling a database of facial features of the patient relative to positions of TMS coils for delivering the TMS therapy.

10. The method of claim 9, further comprising placing markers on the TMS coils that are visible in the optical 3D scan of the head shape of the patient.

11. The method of claim 9, wherein the database of facial features of the patient relative to positions of TMS coils is used to improve consistency of TMS coil placement from one TMS session to another TMS session.

12. The method of claim 11, further comprising use of a display to facilitate positioning of the TMS coils in accordance with the database.

13. The method of claim 9, wherein the facial features comprise facial landmarks.

14. The method of claim 9, wherein the facial features comprise a facial point cloud.

* * * * *